United States Patent
Chakraborty et al.

(10) Patent No.: US 10,577,305 B1
(45) Date of Patent: Mar. 3, 2020

(54) PROCESS FOR THE PRODUCTION OF ESTERS

(71) Applicant: Eastman Chemical Company, Kingsport, TN (US)

(72) Inventors: Sumit Chakraborty, Johnson City, TN (US); Steven J. Adams, Gray, TN (US); Robert Thomas Hembre, Johnson City, TN (US); Scott Donald Barnicki, Kingsport, TN (US); David Alan Jenkins, Jonesborough, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/188,930

(22) Filed: Nov. 13, 2018

(51) Int. Cl.
| | |
|---|---|
| C07C 67/44 | (2006.01) |
| C07C 67/39 | (2006.01) |
| B01J 31/18 | (2006.01) |
| B01J 31/24 | (2006.01) |
| B01J 31/22 | (2006.01) |
| C07C 69/003 | (2006.01) |

(52) U.S. Cl.
CPC ........... *C07C 67/44* (2013.01); *B01J 31/1815* (2013.01); *B01J 31/2295* (2013.01); *B01J 31/2404* (2013.01); *C07C 67/39* (2013.01); *B01J 2231/46* (2013.01); *B01J 2531/821* (2013.01); *C07C 69/003* (2013.01)

(58) Field of Classification Search
CPC ....... C07C 67/00; C07C 67/44; C07C 67/297; C07C 67/39; B01J 2531/821; B01J 2231/46; B01J 2231/76; C07F 15/0046
See application file for complete search history.

(56) References Cited

U.S. PATENT DOCUMENTS

| | | | |
|---|---|---|---|
| 3,215,712 A | 11/1965 | Hübel | |
| 5,892,102 A | 4/1999 | Mikami et al. | |
| 2003/0176300 A1 | 9/2003 | Kodali et al. | |
| 2010/0317824 A1 | 12/2010 | Thoen et al. | |
| 2016/0137582 A1 | 5/2016 | Frey et al. | |
| 2016/0297741 A1* | 10/2016 | Janka | C07C 67/44 |

FOREIGN PATENT DOCUMENTS

| | | | | |
|---|---|---|---|---|
| JP | 08-099933 | * | 4/1996 | ............ C07C 69/54 |
| JP | H11-43463 A | | 2/1999 | |
| JP | 2001-220367 | * | 8/2001 | ............ B01J 23/46 |

OTHER PUBLICATIONS

JP08-99933, Ichikawa, S. et al., Method for manufacturing methacrylic acid ester, 1996, 10 pages (Year: 1996).*
JP2001-220367, Tetsuto, A. et al., Method and catalyst for producing carboxylic acid ester, 2001, 6 pages (Year: 2001).*
Murahashi, S. et al., Ruthenium-catalyzed oxidation transformation of alcohols and aldehydes to esters and Lactones, 1987, J. ORg . Chem, vol. 52, No. 19, pp. 4319-4327 (Year: 1987).*
Co-pending U.S. Appl. No. 16/188,958, filed Nov. 13, 2018; Chakraborty et al.
Co-pending U.S. Appl. No. 16/188,976, filed Nov. 13, 2018; Chakraborty et al.
Blum et al.; "Catalytically Reactive Ruthenium Intermediates in the Homogeneous Oxidation of Alcohols to Esters;" Israel Journal of Chemistry; vol. 24; 1984; pp. 144-148.
Blum et al.; "Catalytically Reactive ($\eta^4$-tetracyclone)(CO)$_2$(H)$_2$Ru and Related Complexes in Dehydrogenation of Alcohols to Esters;" Journal of Organometallic Chemistry; 1985; 282; pp. C7-C10.
Blum et al.; "Structure of "$\eta^4$-Ph$_4$C$_4$CO)(CO)$_3$Ru—a Catalyst Precursor in H-Transfer and Dehydrogenation Reactions of Alcohols;" Inorganica Chimica Acta; 1985; 97; pp. L25-L26.
Chakraborty et al.; "Well-Defined Iron Catalysts for the Acceptorless Reversible Dehydrogenation-Hydrogenation of Alcohols and Ketones;" ACS Catal.; 2014; 4; pp. 3994-4003.
Gianetti et al.; "Nitrous Oxide as a Hydrogen Acceptor for the Dehydrogenative Coupling of Alcohols;" Angew. Chem. Int. Ed.; 2016; 55; pp. 1854-1858.
Grigg et al.; "Oxidation of Alcohols by Transition Metal Complexes—IV;" Tetrahedron; 1981; vol. 37; No. 24; pp. 4313-4319.
Gunanathan et al.; "Applications of Acceptorless Dehydrogenation and Related Transformations in Chemical Synthesis;" Science; 2013; vol. 341; pp. 249.
Gunanathan et al.; "Direct Conversion of Alcohols to Acetals and H2 Catalyzed by an Acridine-Based Ruthenium Pincer Complex;" J. Am. Chem. Soc.; 2009; 131; pp. 3146-3147.
Karmel et al.; "Mono(imidazoline-2-iminato) Actinide Complexes: Synthesis and Application in the Catalytic Dimerization of Aldehydes;" J. Am. Chem. Soc.; 2014; 136; pp. 17180-17192.
Khusnutdinova et al.; "Metal-Ligand Cooperation;" Angew. Chem. Int. Ed.; 2015; 54; pp. 12236-12273.
Kiran et al.; "Single-Step Conversion of Electron-Deficient Aldehydes into the Corresponding Esters in Aqueous Alcohols in the Presence of Iodine and Sodium Nitrite;" Synthesis; 2010; 2; pp. 276-282.
Kuriyama et al.; "Catalytic Hydrogenation of Esters. Development of an Efficient Catalyst and Processes for Synthesising (R)-1,2-Propanediol and 2-(l-Menthoxy)ethanol;" Org. ProcessRes. Dev.; 2012; 16; pp. 166-171.
Lee et al.; "N-Heterocyclic Carbene Catalyzed Oxidative Macrolactonization: Total Synthesis of (+)-Dactylolide;" Angew. Chem. Int. Ed.; 2012; 51; pp. 5735-5738.

(Continued)

*Primary Examiner* — Yate' K Cutliff
(74) *Attorney, Agent, or Firm* — Matthew W. Smith

(57) ABSTRACT

A process for making methyl esters in high yields. The process comprises contacting aliphatic or aromatic aldehydes and methanol with a homogeneous dimeric ruthenium catalyst, to catalyze the dehydrogenative coupling between aliphatic or aromatic aldehydes and methanol. The reaction is highly selective (<99.9%) toward the formation of methyl esters over homoesters and alcohols and operates at temperatures of less than 100° C. for 2-8 hours.

10 Claims, No Drawings

(56) References Cited

OTHER PUBLICATIONS

Murahashi et al.; "Ruthenium-Catalyzed Oxidative Transformation of Alcohols and Aldehydes to Esters and Lactones;" J. Org. Chem.; 1987; 52; pp. 4319-4327.

Murahasi et al.; "Ruthenium Catalyzed Transformation of Alcohols to Esters and Lactones;" Tetrahedron Letters; 1981; vol. 22; No. 52; pp. 5327-5330.

Nielsen et al.; "Towards a Green Process for Bulk-Scale Synthesis of Ethyl Acetate: Efficient Acceptorless Dehydrogenation of Ethanol;" Angew. Chem. Int. Ed.; 2012; 51; pp. 5711-5713.

Rueping et al.; "Asymmetric oxidative Lewis base catalysis—unifying iminium and enamine organocatalysis with oxidations;" Chem. Commun.; 2012; 48; pp. 2201-2203.

Sarkar et al.; "NHC Catalyzed Oxidations of Aldehydes to Esters: Chemoselective Acylation of Alcohols in Presence of Amines;" J. Am. Chem. Soc.; 2010; 132; pp. 1190-1191.

Spasyuk et al.; "Acceptorless Dehydrogenative Coupling of Ethanol and Hydrogenation of Esters and Imines;" Organometallics; 2012; 31; pp. 5239-5242.

Spasyuk et al.; "From Esters to Alcohols and Back with Ruthenium and Osmium Catalysts;" Angew. Chem. Int. Ed.; 2012; 51; pp. 2772-2775.

Spasyuk et al.; "Chemoselective Hydrogenation of Carbonyl Compounds and Acceptorless Dehydrogenative Coupling of Alcohols;" J. Am. Chem. Soc.; 2015; 137; pp. 3743-3746.

Srimani et al.; "Ruthenium Pincer-Catalyzed Cross-Dehydrogenative Coupling of Primary Alcohols with Secondary Alcohols under Neutral Conditions;" Adv. Synth. Catal.; 2012; 354; pp. 2403-2406.

Sumino et al.; "Carbonylation Reactions of Alkyl Iodides through the Interplay of Carbon Radicals and Pd Catalysts;" Acc. Chem. Res.; 2014; 47; pp. 1563-1574.

Toubiana et al.; "The true catalyst in hydrogen transfer reactions with alcohol donors in the presence of $RuCl_2(PPh_3)_3$ is ruthenium(0) nanoparticles;" Catal. Sci. Technol.; 2012; 2; pp. 1644-1653.

Trincado et al.; "Molecular catalysts for hydrogen production from alcohols;" Energy Environ. Sci.; 2014; 7; pp. 2464-2503.

Whittaker et al.; "Nickel-Catalyzed Dehydrogenative Cross-Coupling: Direct Transformation of Aldehydes into Esters and Amides;" Angew. Chem. Int. Ed.; 2015; 54; pp. 1312-1315.

Yang et al.; "Substitution of alcohols by N-nucleophiles via transition metal-catalyzed dehydrogenation;" Chem. Soc. Rev.; 2015; 44; pp. 2305-2329.

Zhang et al.; "Electron-Rich PNP- and PNN-Type Ruthenium(II) Hydrido Borohydride Pincer Complexes. Synthesis, Structure, and Catalytic Dehydrogenation of Alcohols and Hydrogenation of Esters;" Organometallics; 2011; 30; pp. 5716-5724.

Zhang et al.; "Facile Conversion of Alcohols into Esters and Dihydrogen Catalyzed by New Ruthenium Complexes;" J. Am. Chem. Soc.; 2005; 127; pp. 10840-10841.

Office Action dated Nov. 13, 2019 received in co-pending U.S. Appl. No. 16/188,958.

Office Action dated Jun. 21, 2019 received in co-pending U.S. Appl. No. 16/188,976.

Office Action dated Jul. 9, 2019 received in co-pending U.S. Appl. No. 16/188,958.

Eberhardt et al.; "Dehydrogenative Coupling of Aldehydes with Alcohols Catalyzed by a Nickel Hydride Complex;" Organometallics; 2019; 38; pp. 1468-1478.

Johnson et al.; "(Cyclopentadienone)iron Shvo Complexes: Synthesis and Applications to Hydrogen Transfer Reactions;" Organometallics; 2013; 30; pp. 1859-1868.

Thermo Fisher Scientific product page for Acros organics 5.4M (30 wt%) solution in methanol, downloaded from https://www.fishersci.com/shop/products/sodium-methoxide-5-4m-30-wt-solution-methanol-acroseal-acros-organics-2/AC428361000 on Jul. 2, 2019 (Year: 2019).

Yang et al.; "New air-stable iron catalyst for efficient dynamic kinetic resolution of secondary benzylic and aliphatic alcohols;" Tetrahedron Letters; 58; 2017; pp. 2487-2489.

* cited by examiner

PROCESS FOR THE PRODUCTION OF ESTERS

FIELD OF THE INVENTION

The invention generally relates to the field of organic chemistry. It particularly relates to dehydrogenative coupling between aliphatic and aromatic aldehydes and methanol to form methyl esters.

BACKGROUND OF THE INVENTION

Esters are among the most important and abundant functional groups in chemistry and they are widely found in food, pharmaceutical, flavor, and fine and bulk chemical industries. There are a number of classical methods, e.g. reaction with carboxylic acid derivatives, carbonylation and the Tischenko reaction, which can be used to prepare ester compounds. The coupling of aldehydes with alcohols and coupling of two alcohols in the presence of external oxidants can also form esters. An alternative approach is the dehydrogenative coupling of two alcohols or aldehydes with alcohols with the release of $H_2$.

Given the abundance of aldehydes in the marketplace, the dehydrogenative cross-coupling of aldehydes with alcohols could provide an attractive way to directly convert the compound into an ester. However, a big issue facing such cross-coupling reactions is that the metal hydride intermediate, expected to be formed during the dehydrogenation reaction, can readily reduce the aldehydes to alcohols, instead of undergoing desired protonation to form $H_2$.

Such reductions of aldehydes to alcohols also lead to the formation of undesired homoesters. Therefore, these aldehyde-alcohol dehydrogenative coupling reactions often suffer from poor selectivity and as a result downstream separation of the side-products from the desired ester becomes energy-intensive and costly.

A need exists for a thermally stable catalyst which bypasses the formation of alcohols and homoesters and mediates the exclusive formation (selectivity up to >99.9%) of methyl esters between different types of aldehydes and MeOH under mild conditions (<100° C.).

The present invention addresses this need as well as others, which will become apparent from the following description and the appended claims.

SUMMARY OF THE INVENTION

The invention is as set forth in the appended claims.

In one embodiment the invention is a process for preparing esters comprising:
a) combining an aldehyde having the formula $R_1CO$ with an alcohol having the formula $R_2OH$ to form a first mixture;
b) heating the first mixture in the presence of Shvo's catalyst to form an ester having the formula $R_1COR_2O$ and $H_2$;
wherein $R_1$ is a $C_4$ to $C_8$ aliphatic, alicyclic or aromatic group and wherein $R_2$ is a $C_1$ to $C_4$ group.

In another embodiment $R_2$ is selected from the group consisting of methanol, ethanol, propanol, isopropanol, butanol, isobutanol and ethylene glycol.

In another embodiment $R_2$ is methanol.

DETAILED DESCRIPTION OF THE INVENTION

As used herein the following terms have the meaning as described below:

The term "TEG-2EH" refers to triethylene glycol di-ethyl hexanoate.

The term "2EH" refers to 2-ethylhexaldehyde.

The term "2EHOMe" refers to methyl 2-ethylhexanoate.

The term "2EHOH" refers to 2-ethylhexyl alcohol.

The term "2EHOEH" refers to (2-ethylhexyl)2-ethylhexanoate.

The term "2EHenal" refers to 2-ethylhexenal.

The term "iHBu" refers to isobutyraldehyde.

The term "nHBu" refers to n-butyraldehyde.

The term "DMT" refers to dimethyl terephthalate.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 0 to 100 is intended to describe and include all values within the range including sub-ranges such as 0.1-99.9, 60 to 90 and 70 to 80.

It has been surprisingly discovered that an efficient method to form a variety of methyl esters via direct coupling of oxo aldehydes with MeOH in the presence of Shvo's catalyst.

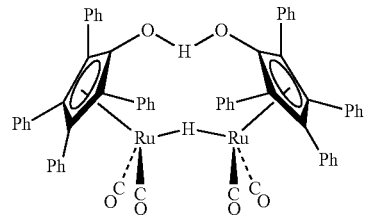

Shvo's Catalyst

Shvo's catalyst (1-Hydroxytetraphenyl-cyclopentadienyl (tetraphenyl-2,4-cyclopentadien-1-one)-mu-hydrotetracarbonyldiruthenium(II)) is available commercially from Millipore Sigma.

We prepared an initial reaction with 2-ethylhexaldehyde (2EH) and methanol (MeOH) as model substrates (Table 1). In the absence of a catalyst, reacting 2-ethylhexaldehyde with excess of methanol (5 equivalents) converted the aldehyde only into a dimethyl acetal in MeOH at 90° C. No ester formation was observed under catalyst-free condition. Next, several homogeneous catalysts were screened in order to facilitate the formation of corresponding methyl 2-ethylhexanoate (2EHOMe) and these results are summarized in Table 1. Simple metal precursor complexes such as [Cp*RhCl$_2$]$_2$, [Cp*IrCl$_2$]$_2$, Ru$_3$(CO)$_{12}$ (Cp*=1,2,3,4,5-pentamethylcyclopentadiene) failed to produce any 2-ethylhexyl alcohol (entries 1-3) and only trace amounts of 2-ethylhexyl alcohol (2EHOH) were produced in these reactions. Well-defined ruthenium and iridium-based homogeneous dehydrogenation catalysts, supported by pincer-type ligands, also showed negligible reactivity and selectivity toward forming methyl 2-ethylhexanoate. For example, Milstein's (PNN)Ru(H)(CO)Cl catalyst 14 (available commercially from Sigma Aldrich) in the presence of KOH afforded methyl 2-ethylhexanoate and 2-ethylhexylalcohol with a relative ratio of 1:1.2 and the overall conversion of 2EH reached to 22% after 6 hours at 90° C. (entry 4). The homoester of 2EH aldehyde, (2-ethylhexyl)2-ethylhexanoate (2EHOEH), was also formed in a considerable amount (11%) during this reaction. In addition to Milstein's catalyst, Takasago's Ru-MACHO15 catalyst (available commercially from Millipore Sigma) afforded 2-ethylhexylalcohol and (2-ethylhexyl)2-ethylhexanoate as major products and methyl 2-ethylhexanoate was only produced in small quantities (entry 5).

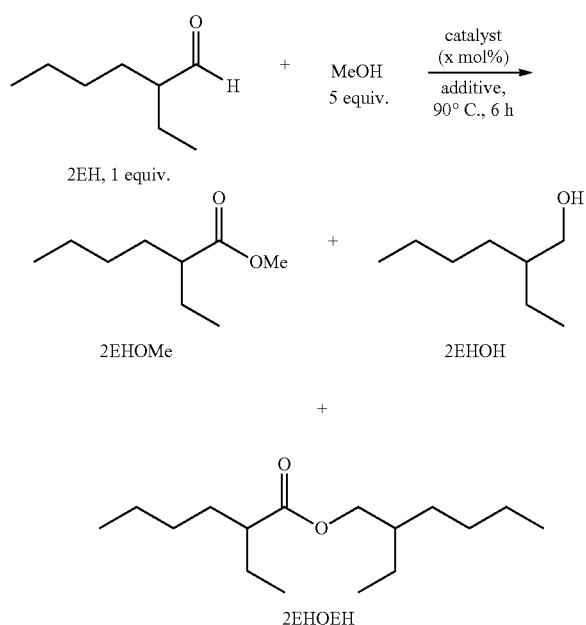

A dimeric ruthenium catalyst, 1-Hydroxytetraphenyl-cyclopentadienyl(tetraphenyl-2,4-cyclopentadien-1-one)-mu-hydrotetracarbonyldiruthenium(II) ($C_{62}H_{41}O_6Ru_2$) commonly known as the Shvo's catalyst, showed excellent reactivity and selectivity toward the formation of methyl esters from corresponding aldehydes via coupling with MeOH. When one equivalent of 2EH aldehyde was treated with five equivalents of MeOH at 90° C. in the presence of 0.5 mol % of Shvo's catalyst, almost exclusive (>99.5 wt %) formation of methyl 2-ethylhexanoate (2EHOMe) was observed after 5 hours (Table 2, entry 1). No starting aldehyde remained after the reaction suggesting 100% conversion within 5 hours. A trace amount of 2EHOEH homoester was also produced as a byproduct in this reaction. Analysis of the crude reaction mixture by gas chromatography (GC) did not detect the formation of 2EHOH, a commonly occurring side-product in such reactions. The catalytic reaction could also be carried out in non-polar aromatic solvents such as toluene, p-xylene or mesitylene without affecting the reactivity and selectivity. Analysis of the volatile components by 1H NMR spectroscopy clearly showed the formation of $H_2$ gas ($\delta$ 4.46, singlet, benzene-d6) from the coupling reaction.

Table 2 summarizes the generality of this coupling method to form methyl esters. Isobutyraldehyde reacted smoothly with methanol to afford methyl isobutyrate in a quantitative yield within four hours (entry 2). A trace amount of isobutyl isobutyrate (IBIB) was also detected by GC.

The coupling reaction between 2-ethylhexenal (2EHenal), a precursor of 2EH, and methanol produced the saturated methyl 2-ethylhexanoate in 97.5 wt % yield (entry 3). The rest of the material accounts for unreacted 2EHenal and 2EHOH. This result indicates that the $H_2$ gas produced during the first 2EHenal-methanol coupling step is used to hydrogenate the C=C double bonds in-situ in the presence of Shvo's catalyst. When methyl cinnamate, an α,β-unsaturated methyl ester, was treated $H_2$ (~3 atm) with 1 mole % of Shvo's catalyst in toluene, complete reduction of the C=C double bond occurred. This direct coupling of 2EHenal with methanol is a highly important discovery because it

TABLE 1

Catalyst Screening Studies for 2EH-MeOH Coupling Reaction.

| Entry | Catalyst (mol %) | Additives (mol %) | Yield of 2EHOMe (%) | Yield of 2EHOH (%) | Yield of 2EHOEH (%) |
|---|---|---|---|---|---|
| 1[a] | [Cp*RhCl$_2$]$_2$ (0.5) | NaOAc(2) | 0 | 3.1 | 0 |
| 2[a] | [Cp*IrCl$_2$]$_2$ (0.5) | NaOAc(2) | 0 | 2.2 | 0 |
| 3[a] | Ru$_3$(CO)$_{12}$ (0.33) | — | 0 | 6.9 | 0 |
| 4 | (Milstein's PNN Ru catalyst structure) | NaOMe(2) | 2.3 | 13.2 | 11.6 |
| 5 | (Ru-MACHO catalyst structure) | NaOMe(2) | 1.1 | 15.3 | 13.9 | eliminates the step for producing 2EH from 2EHenal by hydrogenation with a heterogeneous catalyst (Scheme 1). In addition to the aforementioned substrates aliphatic and aromatic aldehydes like n-butyraldehyde and terephthalaldehyde also afforded corresponding methyl esters in high yields and with minimal to almost no side-product formation.

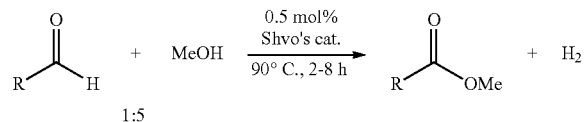

mesitylene-$d_{12}$ solution of Shvo's catalyst at 150° C. for 16 hours and monitored the reaction by $^1$H NMR spectroscopy to study its decomposition products. Under this condition, the catalyst did not undergo decomposition as no additional resonances appeared in the $^1$H NMR spectrum after 16 hours. These experiments collectively suggest that Shvo's catalyst is thermally stable within the temperature range of 90-150° C. and could be reused for catalytic purposes.

The temperature conducive for the TEG-2EH reaction may range, for example, from 120 to 180° C., 125 to 180° C., 130 to 180° C., 135 to 180° C., 138 to 180° C., 120 to 175° C., 120 to 170° C., 120 to 165° C., 120 to 160° C., or 138 to 160° C.

The pressure at which the transesterification reaction may be carried out is not particularly limiting. For example, the

TABLE 2

Ru-Catalyzed Synthesis of Methyl Esters from Aldehydes.[a]

| entry | substrate | product | time (h) | wt% yield |
|---|---|---|---|---|
| 1 | (2-ethylhexanal) | (methyl 2-ethylhexanoate) | 5 | 99.5 |
| 2 | (isobutyraldehyde) | (methyl isobutyrate) | 4 | 99.8 |
| 3 | (2-ethylhex-2-enal) | (methyl 2-ethylhexanoate) | 6.5 | 97.8[b] |
| 4 | (butyraldehyde) | (methyl butyrate) | 2 | 98.3 |
| 5 | (terephthalaldehyde) | (dimethyl terephthalate) | 8 | >99.9 |

[a]Catalytic Conditions: [catalyst] = 0.025 (M), [aldehyde] =5.0 (M), MeOH = 50 mmol, 2 mL, neat conditions, stir speed = 350 rpm, 90° C. (oil-bath temperature). Starting 2EHenal (i.e., <100% conversion) and 2EHOH were detected by GC.

After the catalytic reaction was complete (90° C., 5 hours), Shvo's catalyst was precipitated by adding cold MeOH (~10 mL) and isolated by filtration. A comparison between the isolated material and commercially available Shvo's catalyst by $^1$H NMR spectroscopy revealed that the isolated material was indeed intact Shvo's catalyst.

This result suggests that the catalyst remains unchanged after the first catalytic run. Encouraged by this study, we next carried out a "successive-addition" experiment to test if the catalytic activity of Shvo's catalyst drops or remain unaltered after several catalytic runs (i.e., longer time). The catalytic activity of Shvo's catalyst did not change after five consecutive catalytic runs indicating the catalyst remains robust under our current conditions. To test the thermal stability of Shvo's catalyst above 90° C., we heated a pressure may range from atmospheric to 2 MPa. The reaction may be performed in an open reactor where the produced methanol may be withdrawn as the reaction proceeds. Alternatively, the reaction may be performed in a sealed reactor where the produced methanol remains in the reactor.

The process according to the invention can produce TEG-2EH with yields of at least 90%, at least 95% or at least 99%. The reaction times in which these yields may be achieved include, 8 hours or less, 7 hours or less, 6 hours or less, 5 hours or less, 4 hours or less, 3 hours or less, 2 hours or less, or 1 hour or less.

This invention can be further illustrated by the following examples of preferred embodiments thereof, although it will be understood that these examples are included merely for purposes of illustration and are not intended to limit the scope of the invention unless otherwise specifically indicated.

EXAMPLES

Unless otherwise noted, all the organometallic compounds were handled under a nitrogen atmosphere using standard Schlenk and glovebox techniques. Anhydrous methanol (99.7% grade), toluene and mesitylene (98%) were purchased from Sigma Aldrich and stored with 4 Å molecular sieves. All aldehydes were purchased from commercial sources and freshly vacuum-distilled prior to use. Shvo's catalyst was purchased from Strem Chemicals and used without further purification. Other commercially available catalysts were purchased from respective commercial sources and used without further purification. 1H NMR spectra were recorded on Bruker Avance-500 MHz spectrometers. Chemical shift values in 1H NMR spectra were referenced internally to the residual solvent resonances (δ 7.16 for benzene-d6).

Example 1: Synthesis of Methyl 2-ethylhexanoate from 2-ethylhexaldehyde

Under a nitrogen atmosphere, an oven-dried 100 mL Schlenk tube equipped with a magnetic stir-bar and a Teflon plug was charged with the Shvo's catalyst (54 mg, 50 μmol, 0.5 mol %), 2-ethylhexaldehyde (2EH) (1.6 mL, 10 mmol), and anhydrous methanol (2 mL). The resulting mixture was heated at 90° C. for 5 hours using an oil-bath. The vessel was gradually allowed to come to room temperature and the volatiles ($H_2$ and MeOH vapor) were carefully removed by opening the Teflon plug inside the hood. The liquid sample was analyzed by gas chromatography (GC) to determine the weight percent of methyl 2-ethylhexanoate (99.5 wt %).

Example 2: Synthesis of Methyl Isobutyrate from iHBu

Under a nitrogen atmosphere, an oven-dried 100 mL Schlenk tube equipped with a magnetic stir-bar and a Teflon plug was charged with the Shvo's catalyst (54 mg, 50 μmol, 0.5 mol %), isobutyraldehyde (iHBu) (0.92 mL, 10 mmol, 99% purity), and anhydrous methanol (2 mL). The resulting mixture was heated at 90° C. for 4 hours using an oil-bath. After that the vessel was gradually allowed to come to room temperature and the volatiles ($H_2$ and MeOH vapor) were carefully removed by opening the Teflon plug inside the hood. The liquid sample was analyzed by GC to determine the weight percent of methyl isobutyrate (99.8 wt %).

Example 3: Synthesis of Methyl 2-ethylhexanoate from 2-EHenal

Under a nitrogen atmosphere, an oven-dried 100 mL Schlenk tube equipped with a magnetic stir-bar and a Teflon plug was charged with the Shvo's catalyst (54 mg, 50 μmol, 0.5 mol %), 2-ethyl-2-hexenal (2EHenal) (1.57 mL, 10 mmol), and anhydrous methanol (2 mL). The resulting mixture was heated at 90° C. for 6.5 hours using an oil-bath. After that the vessel was gradually allowed to come to room temperature and the volatiles ($H_2$ and MeOH vapor) were carefully removed by opening the Teflon plug inside the hood. The liquid sample was analyzed by GC to determine the weight percent of methyl 2-ethylhexanoate (97.8 wt %).

Example 4: Synthesis of Methyl Butyrate from nHBu

Under a nitrogen atmosphere, an oven-dried 100 mL Schlenk tube equipped with a magnetic stir-bar and a Teflon plug was charged with the Shvo's catalyst (54 mg, 50 μmol, 0.5 mol %), butyraldehyde (nHBu) (0.94 mL, 10 mmol), and anhydrous methanol (2 mL). The resulting mixture was heated at 90° C. for 2 hours using an oil-bath. After that the vessel was gradually allowed to come to room temperature and the volatiles ($H_2$ and MeOH vapor) were carefully removed by opening the Teflon plug inside the hood. The liquid sample was analyzed by GC to determine the weight percent of methyl butyrate (98.3 wt %).

Example 5: Synthesis of Dimethyl Terephthalate (DMT) from Terephthalaldehyde Under a nitrogen atmosphere, an oven-dried 100 mL Schlenk tube equipped with a magnetic stir-bar and a Teflon plug was charged with the Shvo's catalyst (108 mg, 100 μmol, 1.0 mol %), terephthalaldehyde (1.35 g, 10 mmol, 99% purity), and anhydrous methanol (2 mL). The resulting mixture was heated at 90° C. for 8 hours using an oil-bath. After that the vessel was gradually allowed to come to room temperature and the volatiles ($H_2$ and MeOH vapor) were carefully removed by opening the Teflon plug inside the hood. The liquid sample was analyzed by GC to determine the weight percent of dimethyl terephthalate (>99.9 wt %).

Shvo's catalyst catalyzes the dehydrogenative coupling between aliphatic or aromatic aldehydes and MeOH to afford corresponding methyl esters in high yields. The reaction is highly selective (up to <99.9%) toward the formation of methyl esters and operates under mild conditions (<100° C., 2-8 hours). The catalytic activity and the structure of the catalyst remain unchanged after several catalytic runs.

In the specification, there have been disclosed certain embodiments of the invention and, although specific terms are employed, they are used in a generic and descriptive sense only and not for purposes of limitation, the scope of the invention being set forth in the following claims.

We claim:

1. A process for preparing esters comprising:
   a) combining an aldehyde having the formula $R_1CO$ with an alcohol having the formula $R_2OH$ and a dimeric ruthenium catalyst to form a first mixture;
   b) heating the first mixture to form an ester having the formula $R_1COR_2O$ and $H_2$;
   wherein $R_1$ is a $C_4$ to $C_8$ aliphatic, alicyclic or aromatic group and wherein $R_2$ is a $C_1$ to $C_4$ group, and wherein the weight percent of the ester after step b) is greater than 97 wt. %.

2. The process of claim 1 wherein said catalyst is 1-Hydroxytetraphenyl-cyclopentadienyl(tetraphenyl-2,4-cyclopentadien-1-one)-mu-hydrotetracarbonyldiruthenium(II).

3. The process of claim 1 wherein step b) is conducted at a temperature of less than 100° C. for about 2 hours to about 8 hours.

4. The process of claim 1 wherein the molar ratio of $R_1CO$ to $R_2OH$ in said first mixture is from 1:1 to 1:5.

5. The process of claim 1 wherein the molar amount of catalyst in said first mixture is from about 0.25 mole percent to about 1 mole percent.

6. The process of claim 1 wherein said first mixture further comprises a non-polar aromatic solvent.

7. The process of claim 6 wherein said non-polar aromatic solvent is toluene, p-xylene, mesitylene or a mixture thereof.

8. The process of claim 1 wherein step b) is conducted at a pressure of from atmospheric pressure to 2 ATM.

9. The process of claim 1 wherein $R_2OH$ is selected from the group consisting of methanol, ethanol, propanol, isopropanol, butanol, isobutanol and ethylene glycol.

10. The process of claim 1 wherein $R_2OH$ is methanol.

* * * * *